United States Patent [19]

Kawasaki et al.

[11] Patent Number: 4,931,373

[45] Date of Patent: Jun. 5, 1990

[54] STABLE DNA CONSTRUCTS FOR EXPRESSION OF α-1 ANTITRYPSIN

[75] Inventors: Glenn Kawasaki; Leslie Bell, both of Seattle, Wash.

[73] Assignee: ZymoGenetics, Inc., Seattle, Wash.

[21] Appl. No.: 663,315

[22] Filed: Oct. 22, 1984

Related U.S. Application Data

[63] Continuation of Ser. No. 614,734, May 25, 1984, abandoned.

[51] Int. Cl.$^5$ .................... C12P 21/00; C12P 21/02; C12N 15/00; C12N 7/00
[52] U.S. Cl. .............................. 435/69.2; 435/172.3; 435/255; 435/256; 435/320; 536/27; 935/28; 935/37; 935/69
[58] Field of Search .............. 435/68, 70, 172.3, 317, 435/320, 255, 256; 935/28, 37, 69; 536/27

[56] References Cited

U.S. PATENT DOCUMENTS

4,237,224 12/1980 Cohen et al. .................... 435/68
4,599,311 7/1986 Kawasaki .

OTHER PUBLICATIONS

Bollen et al., 1983, "Cloning and Expression in *E. coli* of Full-Length Complementary DNA Coding for Human α-Antitrypsin", *DNA* vol. 2(4) 255-64.
Walsh et al., 1983, "Cloning of Genes that Complement Yeast Hexokinase & Glucokinase Mutants", *J. Bact.*, vol. 154, 1002-1004.
Carter et al., 1983, "Genetic Control of Cell Proliferation", in *Yeast Genetics*, Spencer et al. (Ed.), Springer-Verlag, pp. 1-28.
Nasmyth et al., 1980, "Isolation of Genes by Complementation in Yeast: Molecular Cloning of a Cell-Cycle Gene", *Proc. Natl. Acad. Sci., vol. 77*, 2119-2123.
Kuruchi et al., *Proc. Natl. Acad. Sci.*, vol. 78, pp. 6826-6830, 1981, "Cloning of Sequence of cDNA coding for α-1-Antitrypsin".
Chandra et al., *Biochem. Biophys. Res. Comm.*, vol. 103, pp. 751-758, 1981.
Strathern et al., *Mol. Biol. of the Yeast Saccharomyces Life Cycle and Inheritance*, pp. 97-142, 1981.
Strathern et al., *Mol. Biol. of the Yeast Saccharomyces Metabolism and Gene Expression*, 1982, pp. 640-651.
Kuo et al., 1983, "Cloning of *Saccharomyces cerevisiae* DNA Replication Gene: Isolation of the CDC 8 Gene . . . ", *Mol. Cell Biol., vol. 3, 1730-37*.
Alber et al., 1982, "Nucleotide Sequence of the Triose Phosphate Isomerase Gene of *S. cerevisiae*", *J. Mol. App. Gen.*, vol. 1, 419-34.
Arendes et al., 1983, "Yeast 2-μm Plasmid DNA Replication in vitro: Purification of the CDC8 Gene Product . . . ", *Proc. Natl. Acad. Sci., vol. 80, 673-77*.
Owen et al., *The New England Journal of Medicine* (1983), pp. 694-698, "Mutation of Antitrypsin to Antithrombin".
Carrell et al., *Nature*, 298 (1982), pp. 329-334, "Structure and Variation of Human α-1-Antitrypsin".

*Primary Examiner*—Robin Teskin
*Attorney, Agent, or Firm*—Seed and Berry

[57] ABSTRACT

Methods are provided for producing α-1-antitrypsin in host cells and for selecting transformed cells comprising the step of transforming the host cell with a DNA molecule comprising a gene which complements a deficiency in the host cell. The host cell is a strain having a deficiency in a function necessary for normal cell growth. The gene in the DNA molecule, such as a plasmid, which complements the deficiency serves as a selectable marker whereby the growth conditions for selection may comprise a conventional complex medium.

6 Claims, 9 Drawing Sheets

SEQUENCE COMPARISON OF S. POMBE AND S. CEREVISIAE GENES FOR TRIOSE
PHOSPHATE ISOMERASE (POT1 AND TPI1)

```
              -150       -140       -130       -120       -110       -100
S. pombe      GGATCCATGCCAACGGTTGCTATCGACGGGGTAAATTGCCCGAAGCTCGGTAATTCCCCT
S. cerevisiae AATTTAGGAGTTTAGTGAACTTGCAACATTTACTATTTTCCCTTCTTACGTAAATATTT -90        -80        -70        -60        -50        -40
S. pombe      TAACTGTGTGACTGTCCGCTACGTTATATATAATGAGCGGACGGGCCAACTCTCGTCTC
S. cerevisiae TTCTTTTTAATTCTAAATCAATCTTTTTCAATTTTTTGTTTGTATTCTTTTCTTGCTTA -30        -20        -10        -1  1              10
S. pombe      TCCCCAACTACATTTCAATAGTAGAACTAGGATCAAA ATG GCA CGT AAA TTC
S. cerevisiae AATCTATAACTACAAAAAACACATACATAAACTAAAA ATG GCT AGA ACT TTC S. pombe                                         MET ALA ARG LYS PHE
S. cerevisiae                                    (Met)        Thr 20         30         40         50         60
S. pombe      TTT GTC GGT GGT AAC TTT AAG ATG AAT GGC TCT TTG GAG TCC ATG
S. cerevisiae TTT GTC GGT GGT AAC TTT AAA TTA AAC GGT TCC AAA CAA TCC ATT S. pombe      PHE VAL GLY GLY ASN PHE LYS MET ASN GLY SER LEU GLU SER MET
S. cerevisiae                         Leu         Lys Gln         Ile 70         80         90        100
S. pombe      AAG ACT ATT ATT GAG GGT TTG AAC ACC ACC AAG CTT AAC GTT GGT
S. cerevisiae AAG GAA ATT GTT GAA AGA TTG AAC ACT GCT TCT ATC CCA GAA AAT S. pombe      LYS THR ILE ILE GLU GLY LEU ASN THR THR LYS LEU ASN VAL GLY
S. cerevisiae     Glu     Val     Arg             Ala Ser Ile Pro Glu Asn 110        120        130        140        150
S. pombe      GAT GTC GAA ACT GTC ATC TTC CCT CAA AAC ATG TAC CTC ATC ACC
S. cerevisiae GTC GAA GTT GTT ATC TGT CCT CCA GCT ACC TAC TTA GAC TAC TCT S. pombe      ASP VAL GLU THR VAL ILE PHE PRO GLN ASN MET TYR LEU ILE THR
S. cerevisiae Val Glu Val Val Ile Cys Pro     Ala Thr Tyr Leu Asp Tyr Ser
```

FIG.—5A

```
                   160           170           180           190
S. pombe      ACC CGC CAA CAA GTC AAG AAG GAT ATT GGC GTT GGT GCC CAA AAC
S. cerevisiae GTC TCT TTG GTT AAG AAG CCA CAA GTC ACT GTC GGT GCT CAA AAC S. pombe      THR ARG GLN GLN VAL LYS LYS ASP ILE GLY VAL GLY ALA GLN ASN
S. cerevisiae Val Ser Leu Val Lys     Pro Gln Val Thr 200           210           220           230       240
S. pombe      GTC TTC GAC AAG AAG AAC GGT GCC TAC ACT GGT GAG AAC AGT GCT
S. cerevisiae GCC TAC TTG AAG GCT TCT GGT GCT TTC ACC GGT GAA AAC TCC GTT S. pombe      VAL PHE ASP LYS LYS ASN GLY ALA TYR THR GLY GLU ASN SER ALA
S. cerevisiae Ala Tyr Leu         Ala Ser         Phe                  Val 250           260           270           280
S. pombe      CAA TCT TTG ATT GAT GCT GGT ATT ACC TAC ACT TTG ACT GGT CAC
S. cerevisiae GAC CAA ATC AAG GAT GTT GGT GCT AAG TGG GTT ATT TTG GGT CAC S. pombe      GLN SER LEU ILE ASP ALA GLY ILE THR TYR THR LEU THR GLY HIS
S. cerevisiae Asp Gln Ile Lys     Val     Ala Lys Trp Val Ile Leu 290           300           310           320       330
S. pombe          TCC GAG CGT CGT ACC ATC TTC AAG GAG TCT GAC GAG TTC GTT GCC
S. cerevisiae TCC GAA AGA AGA TCT TAC TTC CAC GAA GAT GAC AAG TTC ATT GCT S. pombe      SER GLU ARG ARG THR ILE PHE LYS GLU SER ASP GLU PHE VAL ALA
S. cerevisiae                 Ser Tyr     His     Asp     Lys     Ile 340           350           360           370
S. pombe      GAC AAG ACC AAG TTT GCC CTT GAA CAA GGT CTT ACT GTC GTT GCC
S. cerevisiae GAC AAG ACC AAG TTC GCT TTA GGT CAA GGT GTC GGT GTC ATC TGT S. pombe      ASP LYS THR LYS PHE ALA LEU GLU GLN GLY LEU THR VAL VAL ALA
S. cerevisiae                             Gly         Val Gly     Ile Leu 380           390           400           410       420
S. pombe      TGC ATT GGT GAG ACT TTG GCC GAC CGT GAG GCT AAC GAG ACC ATC
S. cerevisiae TGT ATC GGT GAA ACT TTG GAA GAA AAG AAG GCC GGT AAG ACT TTG S. pombe      CYS ILE GLY GLU THR LEU ALA ASP ARG GLU ALA ASN GLU THR ILE
S. cerevisiae                         Glu Glu Lys Lys     Gly Lys     Leu
```

FIG.—5B

```
                            430           440           450           460
S. pombe        ACC GTT GTT GTT CGT CAA TTG AAC GCC ATC GCT GAC AAG GTC CAG
S. cerevisiae   GAT GTT GTT GAA AGA CAA TTG AAC GCT GTC TTG GAA GAA GTT AAG S. pombe        THR VAL VAL VAL ARG GLN LEU ASN ALA ILE ALA ASP LYS VAL GLN
S. cerevisiae   Asp         Glu                     Val Leu Glu Glu     Lys 470           480           490           500           510
S. pombe        AAC TGG TCC AAG ATT GTC ATT GCT TAT GAG CCT GTC TGG GCC ATT
S. cerevisiae   GAC TGG ACT AAC GTC GTT GTC GCT TAC GAA CCA GTC TGG GCC ATT S. pombe        ASN TRP SER LYS ILE VAL ILE ALA TYR GLU PRO VAL TRP ALA ILE
S. cerevisiae   Asp     Thr Asn Val     Val 520           530           540           550
S. pombe        GGT ACT GGT AAG ACT GGC ACC CCT GAG GAA GCT CAA GAG GTT CAC
S. cerevisiae   GGT ACC GGT TTG GCT GCT ACT CCA GAA GAT GCT CAA GAT ATT CAC S. pombe        GLY THR GLY LYS THR GLY THR PRO GLU GLU ALA GLN GLU VAL HIS
S. cerevisiae               Leu Ala Ala                 Asp  -   Asp Ile 560           570           580           590           600
S. pombe        GCT GAG ATC CGC AAG TGG GCT ACC AAC AAG CTT GGT GCA TCT GTT
S. cerevisiae   GCT TCC ATC AGA AAG TTC TTG GCT TCC AAG TTG GGT GAC AAG GCT S. pombe        ALA GLU ILE ARG LYS TRP ALA THR ASN LYS LEU GLY ALA SER VAL
S. cerevisiae       Ser         Phe Leu Ala Ser             Asp Lys Ala 610           620           630           640
S. pombe        GCC GAG GGT CTC CGT GTC ATC TAC GGT GGT TCC GTT ACC GGT GGT
S. cerevisiae   GCC AGC GAA TTG AGA ATC TTA TAC GGT GGT TCC GCT AAC GGT AGC S. pombe        ALA GLU GLY LEU ARG VAL ILE TYR GLY GLY SER VAL THR GLY GLY
S. cerevisiae       Ser Glu     Ile Leu                     Ala Asn     Ser 650           660           670           680           690
S. pombe        AAC TGC AAG GAG TTC CTC AAG TTC CAC GAT ATT GAC GGT TTC TTG
S. cerevisiae   AAC GCC GTT ACC TTC AAG GAC AAG GCT GAT GTC GAT GGT TTC TTG S. pombe        ASN CYS LYS GLU PHE LEU LYS PHE HIS ASP ILE ASP GLY PHE LEU
S. cerevisiae       Ala Val Thr     Lys Asp Lys Ala     Val
```

FIG.—5C

```
                          700         710         720         730
S. pombe      GTT GGC GGT GCT TCT CTC AAG CCT GAA TTC CCT ACT AAC ATT GTT
S. cerevisiae GTC GGT GGT GCT TCT TTG AAG CCA GAA TTT GTT GAT ATC ATC AAC S. pombe      VAL GLY GLY ALA SER LEU LYS PRO GLU PHE PRO THR ASN ILE VAL
S. cerevisiae                                         Val Asp Ile     Asn 740         750    +1      +10      +20      +30
S. pombe      AAT GTT CAC AGC CTT TAA AAACGTGCATAGACGTTTTATTTGGCCGTAAAGCGA
S. cerevisiae TCT AGA AAC TAA         GATTAATATAATTATATAAAAATATTATCTTCTTT S. pombe      ASN VAL HIS SER LEU ***
S. cerevisiae Ser Arg Asn ***

+40      +50      +60      +70      +80      +90
S. pombe      ATGACTTTTTTATTCCTTTAGCTTTTTGTCTTTAATGAATAGGGATTTTTTTATATCCT
S. cerevisiae TCTTTATATCTAGTGTTATGTAAAATAAATTGATGACTACGGAAAGCTTTTTTATATTG +100      +110     +120     +130
S. pombe      AATTTTTTACAAGCAATATTTGATTTATTTTTATTTGCT
S. cerevisiae TTTCTTTTTCATTCTGAGCCACTTAAATTTCGTGAATGT
```

STABLE DNA CONSTRUCTS FOR EXPRESSION OF α-1 ANTITRYPSIN

This is a continuation of Ser. No. 614,734, filed May 25, 1984, now abandoned.

BACKGROUND OF THE INVENTION

The use of microorganisms for the production of useful polypeptide products through recombinant DNA technology is becoming established as an industry. Foreign genetic material may be introduced into a culture of microorganisms, and, given the proper intracellular and extracellular conditions, the desired protein product(s) may be synthesized from the foreign gene(s). Such genetic material is commonly introduced into microorganisms in the form of plasmids, which are autonomously replicating extrachromosomal elements. In order to ensure the maintenance of plasmids within a culture of transformed cells, it has been necessary to grow those cells under special conditions. In the absence of such conditions, the plasmids, which may be inherently unstable, will not be maintained, and the cell populaton will revert to the untransformed state.

Increased plasmid stability and copy number are important to the biotechnology industry as a means of maintaining the production of plasmid-encoded proteins at a consistently high level. Previously reported attempts to increase plasmid stability do not appear to be optimal for commercial application. The introduction of yeast centromeres into ARS-bearing plasmids, while enhancing stability has been shown to markedly decrease plasmid copy number (Clarke and Carbon, *Nature* 287: 504–509, 1980 and Stinchcomb, et al., *J. Molec. Biol.* 158; 157–179, 1982). Linear centrometric yeast plasmids similarly show an inverse relationship between stability and copy number (Murray and Szostak, *Nature* 305: 189–193, 1983).

Plasmids typically contain gene sequences, known as selectable markers, which encode antibiotic resistance or complement nutritional requirements of the host cell. To select for the presence of such plasmids, transformed cells must thus be grown in special media which contain a selective drug or which are depleted for specific nutrients. These media requirements may be both expensive and prohibitive of optimal cell growth rates during the large-scale fermentation process. Many such plasmids have been reported in the literature. Those comprising antibiotic drug resistance genes include pBR322 (Bolivar, et al., *Gene* 2: 95–113, 1977) and its derivatives, such as the pUC vectors (Vieira and Messing, *Gene* 19: 259–268, 1982) which carry a gene for ampicillin resistance; and pBR325 (Prentki, et al., *Gene* 14: 289, 1981) which carries resistance genes for ampicillin, tetracycline, and chloramphenicol. Plasmids which complement host nutrient requirements include the yeast vectors YEp13 (Broach, et al., *Gene* 8: 121–133, 1979), which carries the LEU2 gene; and YRp7' (Stinchcomb, et al., *Nature* 282: 39, 1979), which carries the TRP1 gene.

Alpha-1-antitrypsin is a protease inhibitor, the principal function of which is to inhibit elastase, a broad spectrum protease. Lung tissue in mammals is particularly vulnerable to attack by elastase, therefore alpha-1-antitrypsin deficiency or inactivation may lead to loss of lung tissue elasticity and subsequently to emphysema. Loss or reduction of alpha-1-antitrypsin activity may be a result of oxidation of alpha-1-antitrypsin due to environmental pollutants, including tobacco smoke. Deficiency of alpha-1-antitrypsin may result from one of several genetic disorders. See Gadek, James E., and R. D. Crystal, "Alpha-1-Antitrypsin Deficiency", *The Metabolic Basis of Inherited Disease*, Stanbury, J. B. et al., Ed. McGraw-Hill, N.Y. (1982) pp. 1450–1467; and Carroll, et al., *Nature* 2988, 329–334 (1982).

It is therefore an object of the present invention to provide DNA constructs containing a DNA sequence encoding alpha-1-antitrypsin and, as selectable markers, gene sequences whose products are essential for the viability or normal growth of the host cell on complex media.

It is another object of the present invention to provide transformant strains of microorganisms containing plasmids which are selectable by growth on complex media and which are capable of expressing alpha-1-antitrypsin.

It is a further object of the present invention to provide strains of microorganisms that are deficient in essential functions which may act as hosts for DNA constructs carrying gene sequences which complement these defective essential functions and are capable of expressing alpha-1-antitrypsin.

It is yet another object of the present invention to provide methods for producing alpha-1-antitrypsin is a product of a gene carried on a DNA construct which contains, as a selectable marker, a gene sequence which complements a deficiency in an essential gene in the host microorganism.

Other objects of the invention will become apparent to those skilled in the art.

SUMMARY OF THE INVENTION

According to the present invention, there are provided DNA constructs and appropriates host cells such that the constructs are capable of expressing alpha-1-antitrypsin and maintained at high copy number without the need for special selective media. Growth in such conditions may result in faster growth, greater cell density, and reduced production costs.

The present invention further provides a method for production alpha-1-antitrypsin in a host cell having a deficiency in a function necessary for normal cell growth in complex media, comprising the step of transforming the host cell with a DNA molecule comprising a gene which complements the deficiency and a sequence coding for alpha-1-antitrypsin.

As used herein the term "DNA constructs" means any DNA molecule which has been modified by a man in a manner such that the nucleotide sequences in the molecule are not identical to a sequence which is produced naturally. The term "DNA constructs" also includes clones of DNA molecules which have been so modified. The term "expression vector" is defined as a DNA construct which includes an autonomous site of replication, a site of transcription initiation and at least one structural gene coding for a protein which is to be expressed in the host organism. The expression vector will usually alos contain appropriate control regions such as a promoter and terminator which control the expression of the protein in the host organism. Expression vectors accordin to the present invention will also contain a selection marker comprising an essential gene as described herein.

The term "plasmid" will have its commonly accepted meaning, i.e., autonomously replicating, usually close-looped, DNA.

In the accompanying drawings:

FIG. 5A–5D shows the sequence of the S. pombe POT1 and S. cerevisiae TPI1 genes together with the respective inferred protein sequences. The entire S. pombe TPI protein sequence is given. The sequence of the S. cerevisiae protein is given only where it differs from the S. pombe sequence. The methionine at position 1 in the S. cerevisiae protein sequence is not present in the mature protein.

DETAILED DESCRIPTION

The present invention is based in part upon the discovery that essential genes may be used as selectable markers on DNA constructs such as plasmids which are capable of expressing alpha-1-antitrypsin. An "essential gene" is defined as any gene that codes for a function necessary for cell viability or normal growth on complex media. Complex media are those media in which the nutrients are derived from products whose composition is not well defined, such as crude cell extracts, meat extracts, fruit juice, serum, protein hydrolysates, etc. Hence, to select for a desired transformant according to the present invention, the selection growth medium wil be merely a conventional complex growth medium, not a special medium containing a relatively expensive antibiotic, metal antagonist, or other agent lethal to the untransformed host cell, or lacking one or more specific nutrients required by the untransformed host. Essential genes include, but are not limited to, genes required for cell division, membrane biosynthesis, cell wall biosynthesis, organelle biosynthesis, protein synthesis, carbon source utilization, RNA transcription, and DNA replication.

In order to use an essential gene as a selectable marker on a DNA construct, such as a plasmid, it is necessary to provide an appropriate mutant hose cell strain. Using the one-step gene disruption method of Rothstein (Meth. in Enzymology 101: 202–210, 1983) or the co-transformation procedure described herein, suitable host strains may be constructed which carry deletions in an appropriate essential gene in the genome. Such deletion mutants grow when the mutation is complemented by a function coded by plasmid-borne genetic material. It is preferred that the deletions in the essential gene or genes of the genome of the host comprise substantial segments of the coding region and/or flanking regions. If the mutation or mutations in the essential gene are accomplished in a manner to achieve only point mutations, then there is a likelihood that the mutant hose cell will revert to wild-type mutation or a recombination repair mechanism, thereby reducing or eliminating the selectivity achievable by use of the plasmid-borne gene.

Essential genes often exist in multiple copies (such as histone or ribosomal RNA genes) and/or in multiple, related forms called gene families (such as different hexokinase genes, or different DNA polymerase genes). In such case, these redundant functions may be sequentially mutated to make a host cell which is multiply deficient for a given essential function. However, by using a high copy number plasmid to increase the activity of the gene, a single essential gene on a plasmid may complement multiple host cell deficiencies. A high copy number plasmid is desirable because an increase in copy number of a cloned foreign gene may result in an increase in the production of the protein product encoded by said gene.

The selection for transformants containing high copy numbers of plasmids with essential genes may be accomplished by reducing the expression levels of each plasmid-borne essential gene and/or by reducing the activities of the gene products encoded by the plasmid-borne selectable marker. On approach is to mutate the essential genes such that the transcription and/or translation rates of the genes are reduced or the gene products are altered to have lower specific activities. Another method for decreasing the expression levels of essential genes used as selectable markers is to use a gene from another organism to complement defects in the host cell. Such foreign genes may be naturally defective for expression in a host cell because the signals for transcription and/or translation may be suboptimal in a different species or the gene product may have decreased activity or stability because it is in a foreign cellular milieu.

A broad range of functions necessary for cell viability or normal growth on complex media exists. A defect or deletion in an essential gene may result in lethality, a decrease in the rate of cell division, cessation of cell division, termination of DNA, RNA, or protein synthesis, termination of membrane synthesis, termination of cell wall synthesis, termination of organelle synthesis, defects in sugar metabolism, etc. Examples of essential genes include the CDC (cell divisiion cycle) genes of the yeast *Saccharomyces cerevisiae* (for review see Pringle and Hartwell, "The *Saccharomyces cerevisiae* Cell Cycle", in Strathern, et al., eds., *The Molecular Biology of the Yeast Saccharomyces Life Cycle and Inheritance,* 97–142, Cold Spring Harbor, 1981), the genes coding for functions of the *S. cerevisiae* and *E. coli* glycolytic pathways, and the *SEC (Novick and Schekman, Proc. Nat. Acad. Sci. U.S.A.* 76: 1856–1862, 1979 and Novick, et al., Cell 21: 205–215, 1980) and *INO* (Culbertson and Henry, Genetics 80: 23–40, 1975) genes of *S. cerevisiae.*

One preferred class of essential gene-deficient host cells contains defects in CDC genes known as cdc mutations, which lead to stage-specific arrests of the cell division cycle. Most cdc mutations produce complete blockage of events essential to the cell cycle by affecting either the synthesis or function of the particular CDC gene products. Such mutations may be identified by their effects on events which can be monitored biochemically or morphologically. Most known cdc mutations are conditionally lethal (i.e., temperature sensitive) mutations, which result in the cessation of normal development of mutant cells grown under restrictive conditions. However, the primary defect resulting from a cdc mutation need not be a defect in a stage-specific function per se. For example, continuously-synthesized gene products may have stage specific functions; a defect in the yeast glycolytic gene PYK1 (for the enzyme pyruvate kinase) is allelic to the cell division cycle mutation cdc19 (Kawasaki, Ph.D. Thesis, University of Washington, 1979). This mutation results in cell cycle arrest at the the G1 phase of cells incubated in the typical yeast complex medium YEPD (1% yeast extract, 2% bactopeptone, and 2% dextrose). Thus, whether the cdc mutation results in a defect in a stage-specific function, or whether it causes an inhibition or disabling mutation of a gene product having a stage-specific function, the effect of the defect may be monitored.

Pringle and Hartwell (ibid.) describe the function of some 51 CDC genes. For use in carrying out the present invention, such genes may be isolated from gene libraries by complementation in a strain299 mutation. Gene libraries may be constructed by commonly known procedures (for example, Nasmyth and Reed, *Proc. Natl. Acad. Sci. U.S.A.* 77: 2119–2123, 1980; and Nasmyth and Tatchell, *Cell* 19: 753–764, 1980). Strains carrying the desired cdc mutation may be prepared as described herein, or may be obtained from depositories accessible to the public, such as the American Type Culture Collection and the Berkeley Yeast Stock Center.

A second preferred class of essential genes are those encoding products involved in the glycolytic pathway, including genes coding for metabolic enzymes and for regulatory functions. Examples of glycolytic pathway genes in *S. cerevisiae which have been identified are the glycolysis regulation gene GCR*1 and the genes coding for the enzymes triose phosphate isomerase, hexokinase 1, hexokinase 2, phosphoglucose isomerase, phosphoglycerate kinase, phosphofructokinase, enolase, fructose 1, 6-bisphosphate dehydrogenase, and glyceraldehyde 3-phosphate dehydrogenase. As noted above, the pyruvate kinase gene has been identified and described by Kawasaki. A plasmid containing a yeast phosphoglycerate kinase gene and accompanying regulatory signals has been described by Hitzeman, et al. (*J. Biol. Chem.* 225: 12073–12080, 1980). Isolation and sequencing of the yeast triose phosphate isomerase gene TPI1 has been described by Alber and Kawasaki (*J. Mol. Appl. Genet.* 1: 419–434, 1982) and by Kawaski and Fraenkel (*Biochem. Biophys. Res. Comm.* 108: 1107–1112, 1982).

A particularly preferred glycolytic gene is TPI1, which codes for the yeast triose phosphate isomerase, an enzyme which catalyzes the interconversion of glyceraldehyde-3-phosphate and dihydroxyacetone-3-phosphate and is therefore essential for glycolysis and gluconeogenesis. In *S. cerevisiae* the single genetic locus, TPI1, codes for this function. Cells carrying mutations in TPI1 do not grow on glucose and grow poorly on other carbon sources.

Figure 5A:
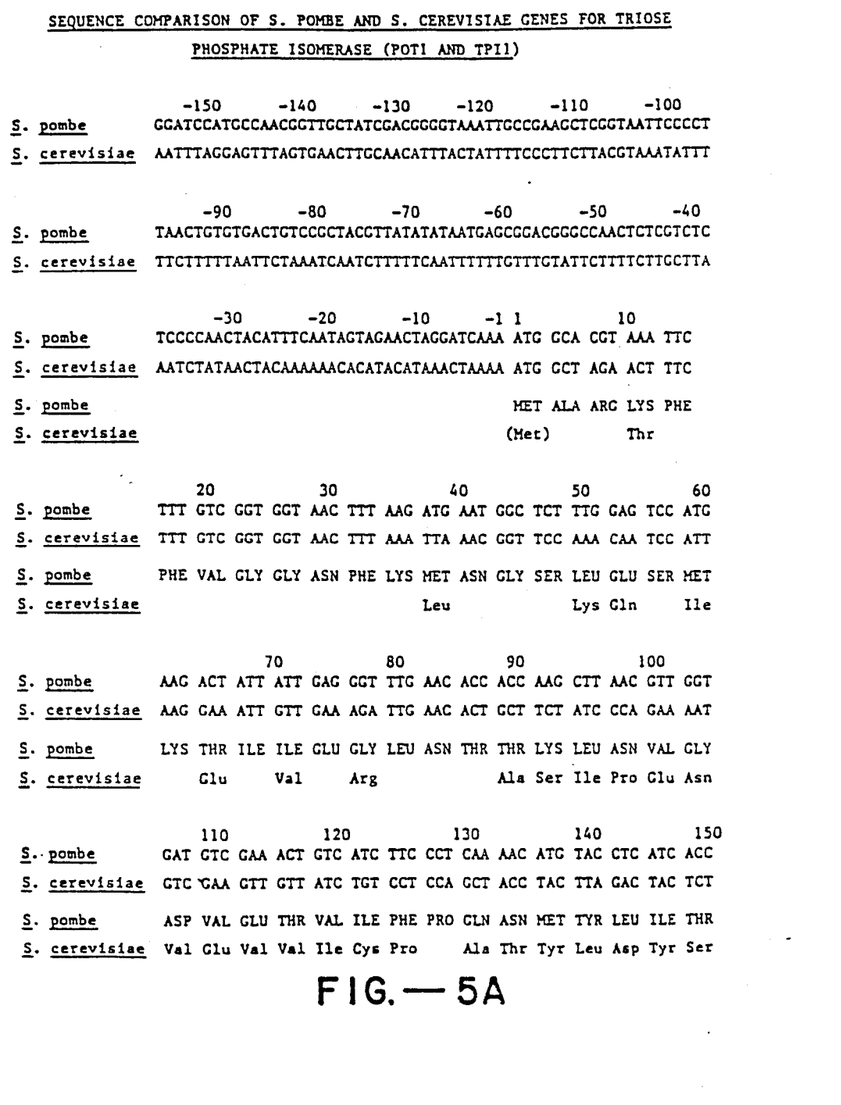
Figure 5D:
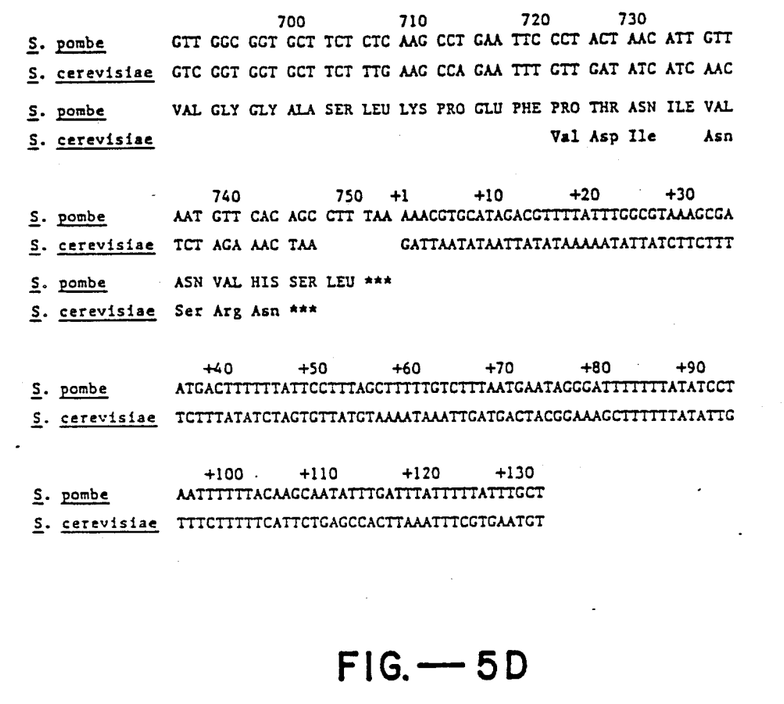

The *S. cerevisiae TPI*1 gene was isolated by complementation of the tpil mutation (Alber and Kawaski, ibid., and Kawaski and Fraenkel, ibid.). The triose phosphate isomerase gene from the fission yeast *Schizosaccharomyces pombe* (POT1) has been isolated by compementation of the same *S. cerevisiae* mutation, and has been sequenced as shown in FIG. 5. Sequencing of the *S. pombe* gene, designated POT1, has demonstrated that the *S. pombe* TPI protein in homologous to the TPI protein of *S. cerevisiae.*

While in the usual case the essential gene which is utilized in the DNA construct (plasmid) will be a wild-type gene from the host species, in some cases it will be preferable to use an essential gene which is foreign to the host cell because the foreign gene may be naturally defective, and thereby selectable to high plasmid copy number. As an example of such a foreign essential gene being used, one of the example herein shows that the *S. pombe* POT1 gene may be effectively used as a selectable marker in an *S. cerevisiae* host.

The DNA constructs according to the present invention containing essential genes as selectable markers will be transformed into mutant host cells which are defective in the function of the essential gene. Properly mutated host cells must either be prepared or, may be readily available from a public depository. Mutation of the wild-type cell to obtain a proper mutant may be accomplished according to conventional procedures. For example, wild-type cells may be treated with conventional mutagenizing agents such as ethane methyl sulfonate and transformed with a plasmid containing an essential gene to identify the colonies where complementation occurs. Alternatively, the genome may be disrupted to create a specific mutation (Rothstein, ibid).

The stability of the plasmid containing the essential gene in the host cell may be dependent on the absence of homologous essential gene sequences in the host cell. The genetic defects in the host ensure that the plasmid will be maintained since growth of the host cell will not occur or will be severely limited by the lack of the essential gene function. Additionally, the integrity of the plasmid itself may be dependent upon the absence of homology between the plasmid-borne essential gene and the corresponding locus in the host genome, because recombination between respective plasmid and genomic loci may cure the cell of both the mutation and the plasmid. Thus, it is preferred that mutation in the host cell genome which inactivates the genomic essential gene be of a substantial nature, i.e., deletions be made from the DNA sequences of the coding section and/or flanking regions of the chromosomal gene. Once this is accomplished, curing of the genomic mutation by recombination is less likely to occur.

The plasmids of the present invention are unexpectedly stable when maintained in the appropriate mutant host cells. A preferred host cell is yeast; however, other eukaryotic cells may be utilized, as well as prokaryotic cells. In the case of yeast cells, the stability of the plasmids according to the present invention appears to exceed even that of yeast plasmids containing centromeres. Circular centromere plasmids are among the most stable plasmids previously reported for yeast, but suffer from an extremely low copy number (Clarke and Carbon, ibid. and Stinchcomb, et al., 1982, ibid.). Linear centrometric yeast plasmids are either unstable or present at low copy number, depending on plasmid length (Murray and Szostak, ibid.). It is therefore an unexpected advantage that improved stability of plasmids bearing an essential gene is achieved.

The POT1 and CDC4 genes are two examples of the utility of essential genes are selectable markers on expression vectors. These two genes belong to a broad class of genes that are required for cell proliferation on complex media. The use of other essential genes may allow for plasmid selection in plant or animal tissue culture which involves complex growth conditions and at the extreme may allow for the maintenance of plasmids in cells receiving nutrition from blood, serum, or sap or living animals or plants.

Data obtained from experiments using plasmids described herein show that human alpha-1-antitrypsin (AT) production is doubled by the use of the *S. pombe* POT1 gene as the selectable marker, when compared to AT production obtained with similar plasmids bearing a traditional auxotrophic selectable marker, LEU2. These results indicate that POT1 containing plasmids are functionally greater in copy number than the non-POT1 plasmids from which they are derived.

The techniques used to produce the DNA constructs, i.e., in particular the plasmids, according to the present invention, involve conventional methods. The essential gene to be utilized in the DNA construct may be isolated from a library by using a labeled DNA probe if the structure of the gene is known, or identified by ligating segments of the DNA library to conventional vectors, transforming the vectors into a mutant cell deficient in the particular essential gene and searching for colonies which are complemented. Once an appropriate DNA fragment containing the essential gene is identified it will be ligated to a vector which contains a DNA sequence coding for the structural protein which will be expressed. The essential gene may be utilized together with its own promoter and other controls necessary for expression within the host organism. Alternatively, a heterologous promotor may be utilized to increase to decrease expression of the essential gene. Methods of ligation of DNA fragments are amply described and are well within the skill of those of ordinary skill in the art to perform.

After preparation of the DNA construct it will be transformed into the host organism under transforming conditions. Techniques for transforming prokaryotes and eukaryotes (including tissue culture cells) are known in the literature.

As described above the host organism must be deficient in the essential function for selection of the essential gene on a plasmid. Mutant host strains are available from conventional depositories or may be made by conventional means for wild-types by mutagenesis and screening for the mutant carrying the proper mutation.

The transformed host may then be selected by growth on conventional complex medium. In the case of yeast, a conventional medium such as YEPD (1% yeast extract, 2% bactopeptone, and 2% dextrose) may be used. The selectable markers comprising essential genes according to the present invention may be used as markers wherever appropriate in any DNA construction and thus it will be recognized that constructs containing the essential gene selection markers according to the present invention have many uses. The following examples are offered by way of illustration of such use, not by way of limitation.

Unless otherwise indicated, standard molecular biology methods were used. Enzymes were obtained from Bethesda Research Laboratories, New England BioLabs, and Boehringer Mannheim Biochemicals, and were used as directed by the manufacturer or as described by Maniatis, et al. (*Molecular Cloning: A Laboratory Manual*, Cold Spring Harbor Laboratory, 1982). *E. coli* cultures were transformed by the calcium chloride method, also disclosed in Maniatis, et al. (ibid). Yeast cultures were transformed by the method of Beggs (*Nature* 275: 104–108, 1978), with modifications as described herein.

EXAMPLE 1

The *S. cerevisiae* CDC4 gene as selectable marker

A. Construction of a stable CDC4-containing plasmid

A yeast genomic library was constructed by partial digestion of yeast DNA with Sau3A, size selection on sucrose gradients, and insertion of the selected fragments into the yeast vector YRp7 which had been digested with BamHI (Nasmyth and Reed, *Proc. Natl. Acad. Sci. U.S.A.* 77: 2119–2123, 1980). A recombinant plasmid containing the CDC4 gene was isolated by transformation of yeast strains GEB5 (MATa cdc4-4 leu2 trp1 lys1 ura1) and GEB7 (MATa cdc4-3 leu2 trp1 lys1) with the library. These strains were derived from strains A364A cdc4-3 and A364A cdc4-4 (Hartwell, et al., *Genetics* 74: 267–286, 1973) by crossing with a strain known to transform at high frequency (K79 [MATα leu2 trp1] (Nasmyth, et al., *Nature* 289: 244–250, 1981; Tatchell, et al., *Cell* 27: 25–35, 1981) followed by backcrossing to high transforming strains (K79 and K80 [MATa leu2 trp1 lys1]) to obtain the cdc-4-3 and cdc4-4 mutations in the desired genetic background (leu2 trp1). Selection of transformants for tryptophan prototrophy and the ability to grow at the restrictive temperature (37°) identified one such plasmid (designated pJY35) which was shown to integrate into the genome and map to the CDC4 locus. Spontaneous plasmid integrants were identified on the basis of their selective growth advantage. This growth advantage is due to the presence, on the original plasmid, of a CDC4-linked gene which is deleterious to cell growth when present at high copy number (i.e., when the plasmid is not integrated into the host genome). In the integrants, the TRP1 plasmid marker was shown to be genetically linked to SUP11, which is linked to CDC4 on chromosome VI (Mortimer and Schild, "Genetic Map of *Saccharomyces cerevisiae*" in Strathern, et al., eds., *The Molecular Biology of the Yeast Saccharomyces cerevisiae Life Cycle and Inheritance*, 641–651, Cold Spring Harbor, 1981). The cdc4-3 complementing region was purified from pJY35 as a 6.4 kb BamHI fragment and was joined, using T4 DNA ligase, to the vector YRp7 (Struhl, et al., *Proc. Natl. Acad. Sci. U.S.A.* 76: 1035–1039, 1979) which had been cleaved with BamHI. This construct is known as pJY51, and is illustrated in FIG. 1.

Figure 1:
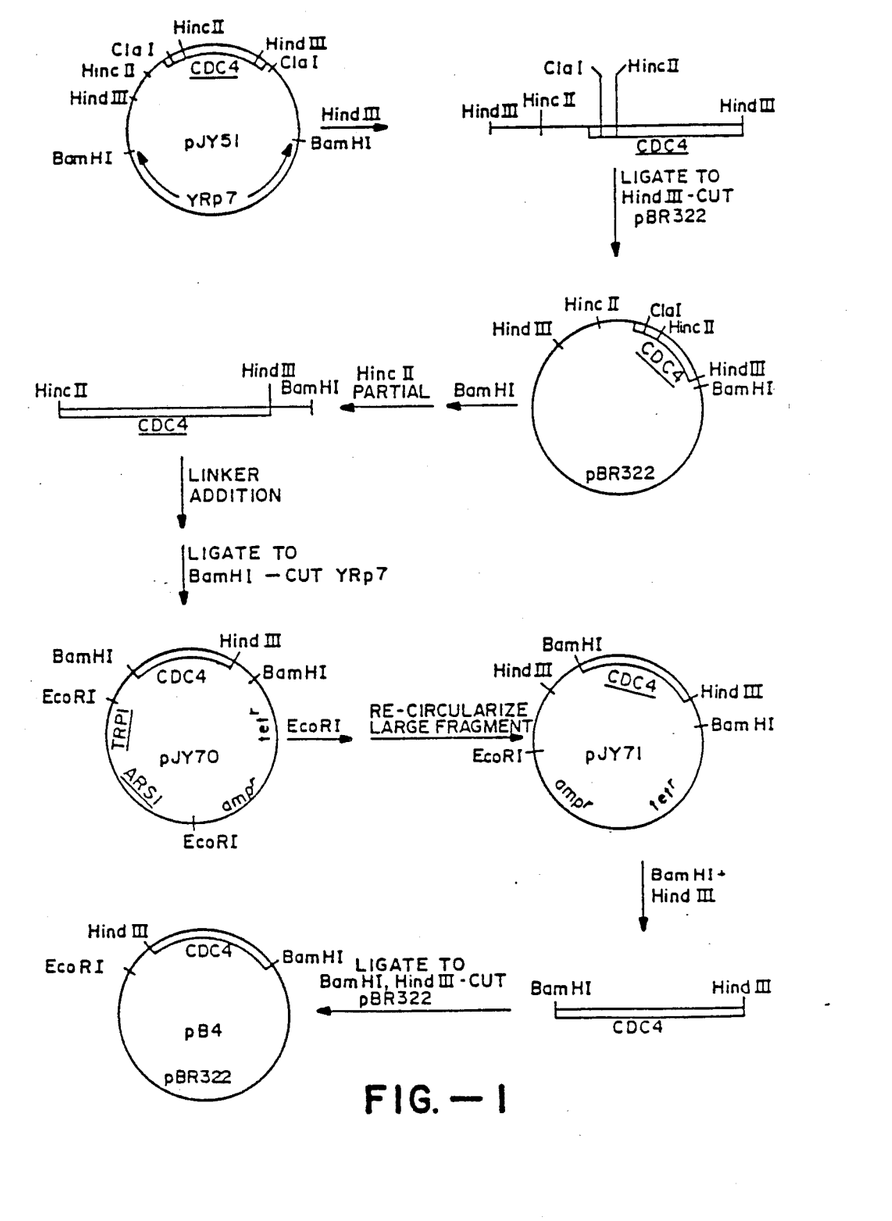
FIG. 1 illustrates the construction of plasmid pB4.

Referring to FIG. 1 to CDC4 coding region was purified away from flanking genomic DNA sequences in the following manner. Plasmid pJY51 was cleaved with HindIII and the 3.6 kb fragment comprising the CDC4 region was subcloned in the bacterial plasmid pBR322. This construct was digested to completion with BamHI, partially digested with HincII, and the ca. 2.3 kb CDC4-containing fragment was purified. The HincII fragment end was converted to a BamHI end by the addition of linker sequences (sequence:5'CC-GGATCCGG3') (obtained from Collaborative Research) and subsequent digestion with BamHI to remove excess linkers. The resulting fragment, comprising approximately 1.9 kb of the CDC4 gene, was inserted into the BamHI site of YRp7 to produce plasmid pJY70. This plasmid was shown to complement the cdc4-3 mutation as described above. Although the 1.9 kb fragment lacks small portions of both the 5'- and 3'-coding regions of the CDC4 gene, it surprisingly complements the temperature-sensitive defect. Presumably, transcription and translation of the CDC4 sequence is controlled by sequences located in the pBR322 regions of the plasmid, allowing for production of a functional gene product.

Plasmid pJY70 was cleaved with EcoRI to remove the yeast TRP1 and ARS1 sequences and was re-ligated, yielding a hybrid plasmid comprising pBR322 and CDC4 sequences. This plasmid is known as pJY71, and is illustrated in FIG. 1.

Figure 2:
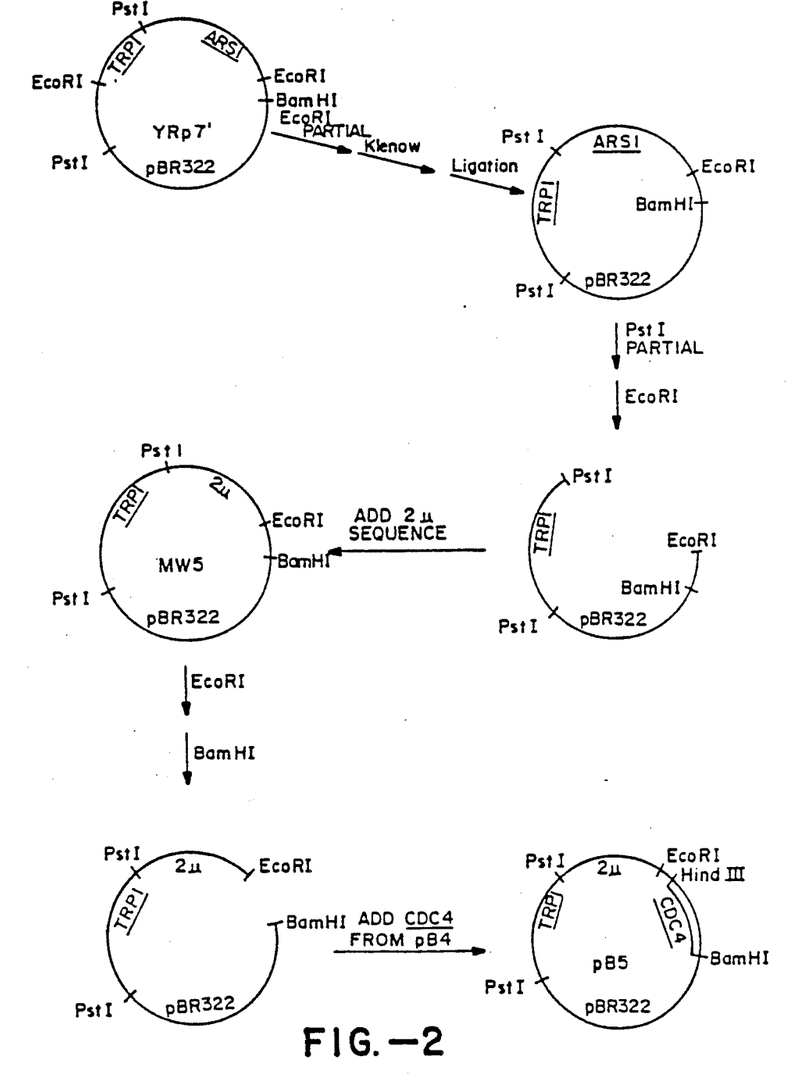
FIG. 2 illustrates the construction of plasmid pB5.

The 1.9 kb yeast sequence was purified from pJY71 as a BamHI-HindIII fragment. This fragment was joined to pBR322 which had been linearized by digestion with BamHI and HindIII, to produce the plasmid pB4, and is illustrated in FIG. 1. The CDC4 region was re-isolated from pB4 for insertion into a high copy number yeast vector. Such a vector will contain an origin of replication of the yeast $2\mu$ plasmid, and one or more restriction enzyme cleavage sites which will serve as cloning sites for foreign genes of interest. Preferably such sites will be unique sites on the plasmid. A preferred vector is MW5, which comprises the yeast $2\mu$ plasmid replication origin and unique EcoRI and BamHI cloning sites. Referring to FIG. 2 plasmid MW5 was derived from plasmid YRp7' (Stinchcomb, et al., *Nature* 282: 39–43, 1979) by partial digestion with EcoRI to cleave, on average, one of the two EcoRI sites per molecule. The resulting unpaired ends of the linear molecules were filled in using DNA pllymerase I (Klenow fragment) and the resulting blunt ends were re-joining using T4 DNA ligase. The resulting plasmid which retained the EcoRI site adjacent to the ARS1 sequence was then selected. The ARS1 sequence was removed by digestion with PstI and EcoRI, and replaced with the PstI-EcoRI fragment of plasmid YEp13 (Broach, et al., *Gene* 8: 121–133, 1979) which comprises the replication origin of yeast $2\mu$ DNA. The resulting plasmid, designated MW5, is illustrated in FIG. 2.

To construct the final CDC4-containing stable plasmid, MW5 was cleaved with EcoRI and BamHI. The CDC4 fragment was purified from plasmid pB4 by digesting the plasmid with BamHI and EcoRI. The two fragments were joined, using T4 DNA ligase, and the chimeric molecules so produced were transformed in E. coli strain RRI (Nasmyth and Reed, ibid.) with selection for ampicillin-resistant, tetracycline-sentitive colonies. Plasmid pB5 (shown in FIG. 2), isolated from one such colony, comprises the yeast $2\mu$ replication origin, pBR322 plasmid sequences, the selectable marker TRP1, 1.9 kb of the yeast CDC4 coding sequence, and a unique EcoRI cloning site.

B. Construction of a plasmid for disruption of host CDC4 gene

The stability, in a transformed host, of the CDC4-containing plasmid according to the present invention is dependent on the lack of a functional CDC4 gene in the host. It is further desirable that no homology exists between the host genome and the CDC4-containing stable plasmid in order to prevent recombination between plasmid and chromosomal DNA's. To obtain a yeast strain having a suitably deleted CDC4 locus, a yeast host containing the wild-type CDC4 gene may be transformed with a linearized plasmid fragment having a "disrupted" CDC4 gene (Rothstein, ibid.). The linearized plasmid fragment is a preferred transforming agent because the free ends of the fragment may enhance recombination which the CDC4 region. Such a plasmid fragment will have intact CDC4 flanking regions at its ends to facilitate recombination with the intact genomic CDC4 locus. The genetic material inserted between the CDC4 flanking regions of the plasmid fragment will code for a phenotypic characteristic which can be selected in the transformed host (a selectable marker such as TRP1 or LEU2). The disrupting plasmid will preferably also lack a yeast origin of replication in order to select for the integration of the disrupted CDC4-selectable marker sequence into the host genome. Following transformation with the linearized plasmid genetic recombination results in the substitution of the disrupted sequence for the genomic sequence of the host. Cells in which the CDC4 gene has now been deleted are then selectable according to the marker used in the disruption.

A method for a one-step disruption of a host genome is described by Rothstein (ibid.). As described above, disruption is performed with the added improvement of co-transforming a host strain with an intact stable plasmid and a linearized plasmid such that in addition to achieving disruption of the host genome, transformation of the host with the stable plasmid is also effected.

Figure 3:
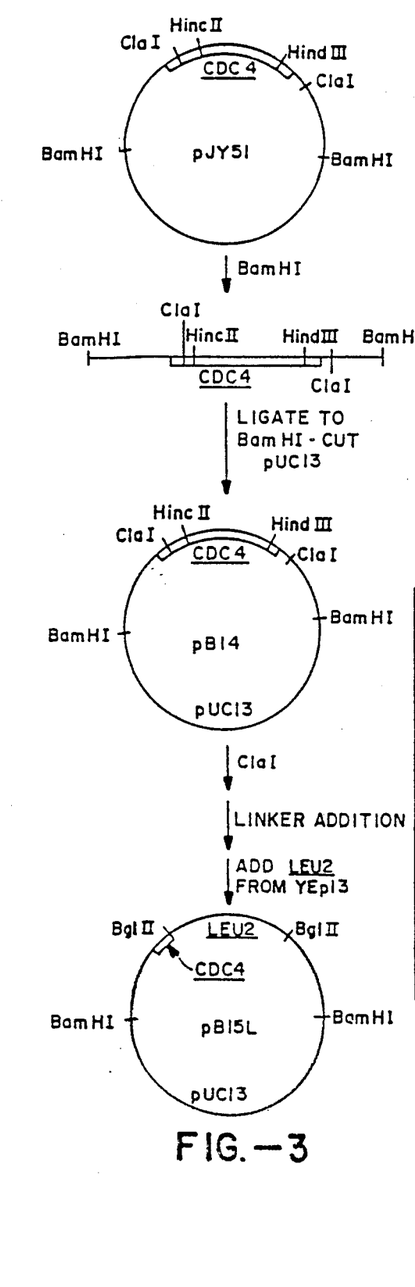
FIG. 3 illustrates the construction of plasmid pB15L.

A preferred plasmid for disruption of the host CDC4 locus is pB15L, shown in FIG. 3. It comprises the yeast LEU2 gene inserted between the flanking regions of CDC4, and the vector pUC13 (Vieira and Messing, *Gene* 19: 259–268, 1982 and Messing, *Meth. in Enzymology* 101: 20–77, 1983). When linearized at the junctions of yeast and vector sequences and transformed into a suitable yeast host strain, the plasmid produces a deletion of CDC4 in the host genome resulting from the substitution of the LEU2 sequence for the CDC4 region. In a host strain auxotrophic for leucine, disrupted transformants may then be selected on the basis of leucine prototrophy.

To construct plasmid pB15L, a 6.4 kb fragment comprising the CDC4 gene and its 5'- and 3'-flanking regions was purified from a BamHI digest of pJY51. This fragment was inserted into BamHI-digested pUC13 to produce the plasmid pB14. Most of the CDC4 coding region was removed by digesting pB14 with ClaI and purifying the larger fragment which comprises the pUC13 and CDC4 flanking sequences. The fragment ends were modified by the addition of XhoI (BglII) "smart" linkers (Worthington Diagnostic), and the 2.8 kb BglII LEU2 fragment of YEp13 (Broach, et al., *Gene* 8: 121–133, 1979) was joined to the resultant cohesive termini. DNA so prepared was used to transform *E. coli* strain RRI. TRansformants were selected on the basis of leucine prototrophy, since the yeast LEU2 sequence complements the leuB defect in the *E. coli* host. Plasmid pB15L was purified from one such transformed colony.

Plasmid pB15L comprises only about 50 base pairs of the 5' end of the CDC4 coding sequence in addition to the 5' and 3' flanking sequences. A comparison of the maps of plasmids pB5 and pB15L shows a lack of homology between their respective CDC4 sequences as the junction points of the CDC4-LEU2 gene fusion of pB15L are located outside the region of the CDC4 fragment present in pB5. This lack of homology prevents recombination between pB5 and the disrupted CDC4 locus in the host cell.

C. Co-transformation of *S. cerevisiae*

To simultaneously delete the genomic CDC4 gene and introduce plasmid pB5, yeast cells were co-transformed with BamHI-cleaved pB15L and intact plasmid pB5. The host strain to be used in the transformation should be auxotrophic for tryptophan and leucine in order to select simultaneously for plasmid pB5 and the genomic CDC4 disruption. Strain A2.7.c (MATα cdc4-3 trp1 leu2-2,112 lys1 his3-11,15 can1 obtained from a cross of strain A2 (MATα leu2-2,112 his3-11,15 can1; see Szostak, *Meth. in Enzymology* 101: 245–252, 1983) with strain GEB7 (see Example 1A) was used.

In a typical co-transformation experiment, 10 ml of a culture of *S. cerevisiae* A2.7.c in log phase growth were transformed with approximately 6 μg of BamHI-digested pB15L, 1 μg pB5, and 10 μg calf thymus DNA as carrier. Transformation conditions were as described by Beggs (ibid.). Cells were plated on a medium lacking leucine and tryptophan. They were grown overnight at 22° and shifted to 37°. Approximately 30 colonies were obtained. The control transformation with pB5 alone and selection for tryptophan prototrophy produced approximately 1,000 transformants.

Six co-transformed colonies were analyzed to verify the disruption of the CDC4 locus and to test the stability of the pB5 plasmid. Genomic DNA was isolated from co-transformants by the method of Abraham, et al. (*Cold Spring Harbor Symposium Quant. Biol.* 47: 989–998, 1983) and was digested with EcoRI and BamHI, electrophoresed on an agarose gel, and transferred to nitrocellulose (Southern, *J. Mol. Biol.* 98: 503–517, 1975). The blot was probed with the 2.5 kb BamHI-HindIII fragment from the 5′ flanking region of CDC4 present in pB15L but absent from pB5.

Figure 4:
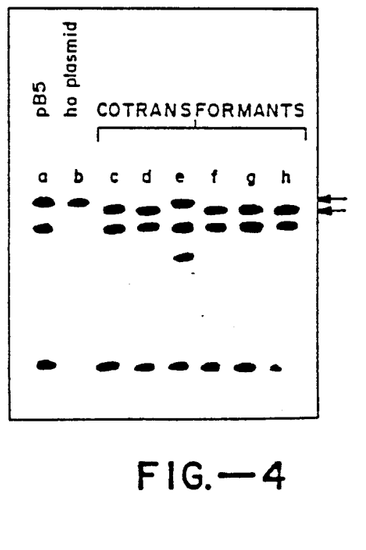
FIG. 4 shows a Southern blot of DNA from S. cerevisiae strain A2.7.c co-transformed with plasmids pB5 and pB15L. The blot was probed with a 2.5 kb BamHI-HindIII fragment from the 5' flanking region of CDC4 in order to test for disruption of the genomic CDC4 locus. Lane a contains DNA from cells transformed with pB5 alone; Lane b, untransformed cells; Lanes c-h, co-transformants. Arrows indicate the genomic fragments hybridizing to the probe.

FIG. 4 shows that the probe hybridized to a 6.4 kb fragment of DNA from untransformed cells (lane b); there is no EcoRI site within this 6.4 kb BamHI fragment. As the LEU2 sequence contains an EcoRI site, disruption of the CDC4 locus will result in a reduction in size of the hybridizing band (indicated by arrows in FIG. 4). This is the case for the transformants represented in lanes c, d, f, g, and h. Lane e shows a somewhat different pattern and retains the genomic-size band, indicating that deletion of the genomic CDC4 did not occur. (The smaller bands seen in lanes c through h are due to contamination of the gel-purified probe, as shown by the patterns of the controls in lanes a and b.)

The six co-transformants were tested for plasmid stability by growing on complex medium (YEPD). Cells were grown for 30 generations in liquid YEPD at 25°, then plated on YEPD at 25°, and replica plated onto YEPD at 37°, tryptophanless medium, and leucineless medium. Results summarized in Table 1 indicate that all co-transformants except #3 were 100% stable for the plasmid markers on complex media. (Isolate number 3 is the same co-transformant represented in lane e of FIG. 4).

Further stability tests were performed on two co-transformants, numbers 1 and 2. Testing was performed on 663 and 681 colonies respectively. After growth for 30 generations on YEPD at 30°, all colonies were prototrophic for tryptophan and leucine.

Co-transformant #1 was tested for growth rate at 22° and was found to grow at the same rate as an untransformed A2.7.c control.

Co-transformant #1 has been designated BELL1. It has been deposited with ATCC under accession number 20698.

EXAMPLE 2

*Schizosaccharomyces pombe* POT1 gene

A. *S. pombe* POT1 gene as a selectable marker

The *Saccharomyces cerevisiae* TPI1 gene codes for the triose phosphate isomerase protein and has been obtained by complementing the tpi1 deficiency (Kawasaki and Fraenkel, ibid.; Alber and Kawasaki, ibid.). Surprisingly, the homologous gene from *S. pombe* has been isolated by complementing the same *S. cerevisiae* tpi1 mutation. The *S. pombe* TPI gene, designated as POT1 (for pombe triose phosphate isomerase), has been cloned from a library described by Russell and Hall (*J. Biol. Chem.* 258: 143–149, 1983) which contains genomic *S. pombe* DNA that has been partially digested with Sau3A and inserted into the vector YEp13. A preliminary DNA sequence (by the method of Maxam and Gilbert, *Meth. in Enzymology* 65: 497–559, 1980) has demonstrated that the POT1 gene codes for the TPI protein and said protein is homologous with TPI proteins from other organisms (see Alber and Kawasaki, ibid.). This POT1 DNA sequence is given in FIG. 5, together with the *S. cerevisiae* TPI1 DNA sequence and the respective protein sequences.

The *S. pombe* POT1 gene is preferred in this example over the *S. cerevisiae* TPI1 gene as a selectable marker in *S. cerevisiae*. Foreign genes, such as POT1 in *S. cerevisiae*, may not function well in an alien host cell and therefore may necessitate a higher copy number to complement a host cell defect. Also the selectable POT1 gene on a yeast plasmid allows for the use of the endogenous TPI1 promoter and TPI1 terminator (control regions that show no homology with POT1) for expression of commercially important genes on the same vector. Because POT1 and the flanking regions of TPI1 show no homology, intramolecular recombination and subsequent plasmid instability are reduced. Finally, the POT1 gene is not likely to recombine with the *S. cerevisiae* chromosomal DNA because it shares little homology at the DNA level with the TPI1 sequence and much of the TPI1 gene has been deleted in the host strains. Thus, POT1 containing plasmids may remain at high copy numbers which are desirable for the elevated expression of foreign genes of commercial interest in yeast.

A plasmid comprising the POT1 gene was identified from the *S. pombe* library of Russell and Hall (ibid.) by complementation of the tpi1 mutation in *S. cerevisiae* strain N587-2D (Kawasaki and Fraenkel, ibid.).

Figure 6:
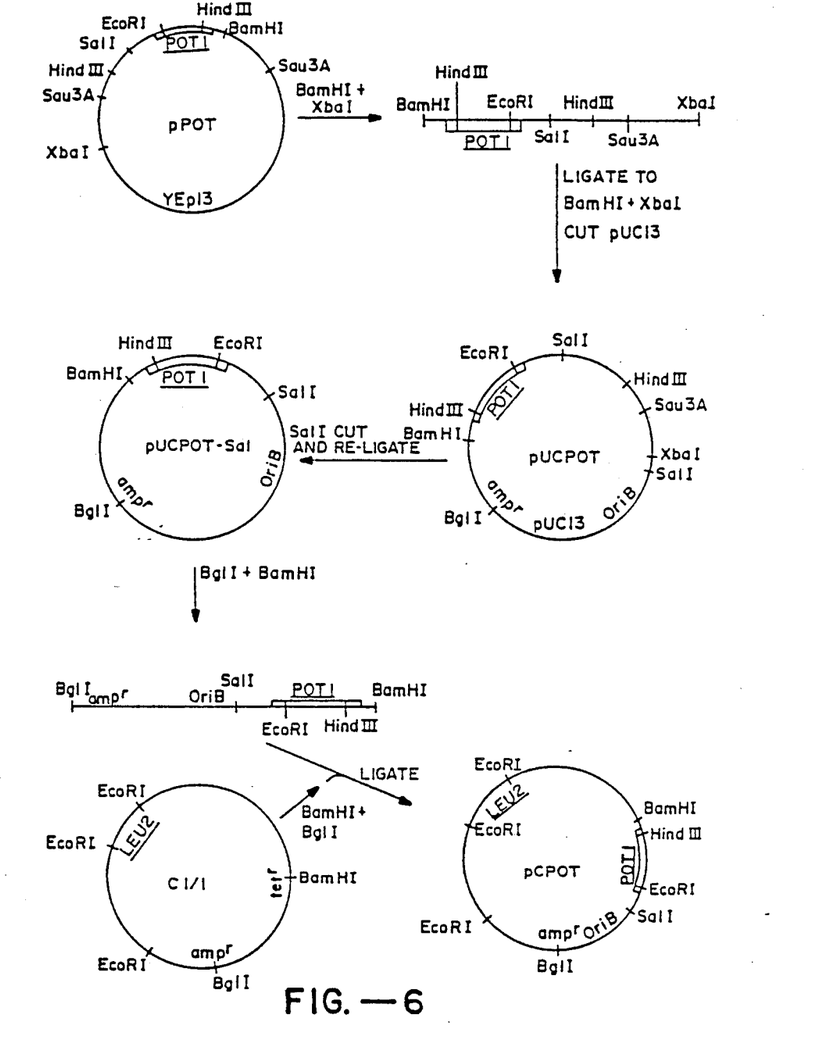
FIG. 6 illustrates the construction of the plasmid pCPOT.

A restriction map of this plasmid, pPOT, is depicted in FIG. 6. Because pPOT contains the vector YEp13, it is inherently unstable, since it lacks replication functions necessary for the maintenance of 2-micron plasmids in yeast. Therefore, the POT1 gene may be moved into more competent vectors, such as C1/1 and related vectors that contain the entire 2-micron plasmid sequences. Plasmid C1/1 was derived from pJDB248 (Beggs, *Nature* 275: 104–109, 1978) and pBR322 as described in Example 3 herein. It contains all of the yeast 2-micron plasmid DNA, a selectable LEU2 gene, and pBR322 sequences.

The POT1 gene was isolated from pPOT as a BamHI-XbaI restriction fragment of nearly 3,400 base pairs and was inserted into the corresponding polylinker sites of pUC13. The resulting plasmid is pUCPOT, a partial restriction map of which is shown in FIG. 6.

The pUCPOT plasmid was cut with SalI and religated to delete about 1,800 base pairs of *S. pombe* and *S. cerevisiae* DNA. This resulting pUCPOT-Sa1 plasmid is illustrated in FIG. 6.

The POT1 gene was put into C1/1 in the following manner. As both C1/1 and pUCPOT-Sa1 have a BglI site in the ampicillin resistance gene and a unique BamHI site at some other location, the POT1 fragment of pUCPOT-Sal may be substituted for a portion of the pBR322 region of C1/1. C1/1 was cut with BglI and BamHI to liberate a large fragment of nearly 7,700 base pairs that contains part of the amp$^r$ gene, all 2-micron DNA, and the LEU2 gene. Likewise, pUCPOT-Sal was cut with BglI and BamHI to liberate a fragment of nearly 3,400 base pairs that contains the other portion of the amp$^r$ gene and the POT1 gene. These two fragments were ligated to form pCPOT, which contains a "restored" selectable amp$^r$ gene, the POT1 gene, the LEU2 gene, all 2-micron DNA, and the bacterial origin of replication region from pUC13 (the bacterial origin region from pUC13 allows for a higher copy number of plasmids in *E. coli* than does the origin regin of pBR322).

*E. coli* strain HB101 transformed with pCPOT has been deposited with ATCC under accession number 39685.

The POT1 gene may also be inserted into C1/1-derived vectors by a similar construction. For example, the plasmid pFAT5 (FIG. 7) contains an expression unit for the production of human alpha-1-antitrypsin (AT) inserted into C1/1. This expression unit, prepared as described in Example 4 consists of the TPI1 promoter, the AT cDNA sequence, and the TPI1 transcription terminator. A restriction map of pFAT5 is given in FIG. 7.

pFAT5 was cut with BglI and BamHI to liberate a fragment (2,200 base pairs) that contains the AT gene and the TPI1 terminator. Also liberated is a BglI-BamHI fragment which is identical to the C1/1 BglI-BamHI fragment described above, except that the fragment from pFAT5 contains an additional 900 base pairs that comprise the TPI1 promoter. This latter pFAT5 piece and the pUCPOT-Sal 3400 bp BglI-BamHI fragment (described above) are ligated to form the plasmid pFPOT, which has the restriction map shown in FIG. 7.

The vector pFPOT was cut at the unique BamHI site to allow for the insertion of the 2,200 base pair AT gene and TPI1 terminator fragment from pFAT5. The cloning of the 2,200 base pair fragment in the proper orientation into pFPOT allows for the expression of human AT in this yeast vector. The properly ligated product is designated pFATPOT, whose restriction map is given in FIG. 7.

B. Disruption of host TPI gene

The *Saccharomyces cerevisiae* TPI1 gene has been cloned and sequenced (Kawasaki and Fraenkel, ibid. and Alber and Kawasaki, ibid.). The plasmid pTPIC10, comprising the structural gene for the TPI protein, has been described in Alber and Kawasaki (ibid.). A BglII site exists at DNA position 295 in the coding region of TPI1, and another BglII site is located approximately 1,200 base pairs away in the 5' flanking region. These BglII sites are convenient cloning sites for deleting part of the TPI1 gene and for inserting another gene, such as the yeast LEU2 gene. Such a construct can be used to produce a disruption of the genomic TPI1 locus in a transformed host.

At approximately -1800 in the 5' flanking region of TPI1 is a PstI site. In pTPIC10, therefore, the TPI1 gene is flanked by a PstI site on the 5' side and by a SalI site (in the tet$^r$ gene) on the 3' side. This PstI-SalI fragment which contains TPI1 was inserted into pUC13 at the PstI and SalI sites to produce pUCTPI. A restriction map of the PstI-SalI insert (into pUC13) is given in FIG. 8.

Figure 8:
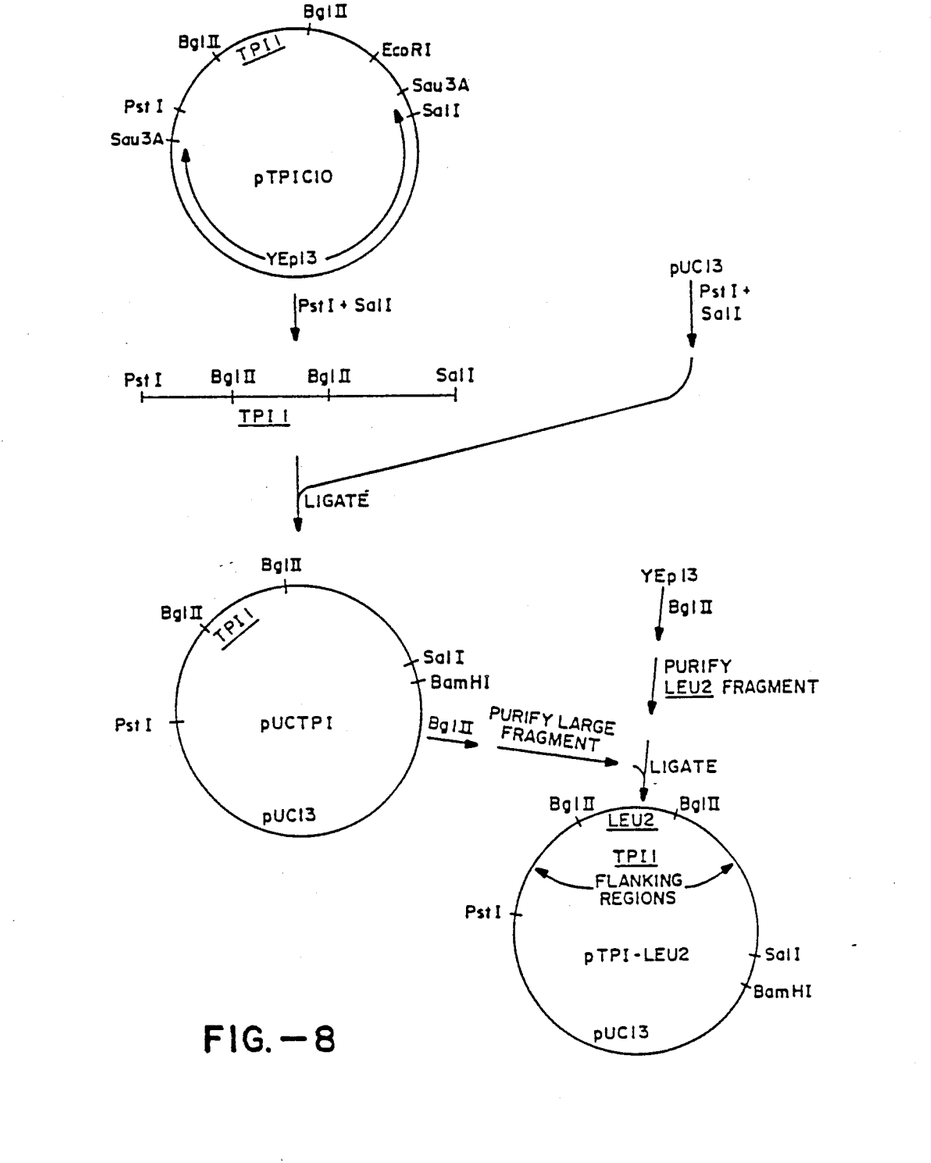
FIG. 8 illustrates the constructon of the plasmid pTPI-LEU2.

The plasmid pUCTPI was then cut with BglII and the two DNA fragments were separated by electrophoresis. The larger fragment was purified and phosphatased to prevent self-ligation. Into the BglII sites of this DNA was ligated the yeast LEU2 gene, which was removed from the plasmid YEp13 (Broach, et al., Gene 8: 121-133, 1979) as a BglII fragment. The resulting plasmid was pUCTPI-LEU2, which carries a partial deletion of TPI1 and an insertion of LEU2. pUCTPI-LEU2 is depicted in FIG. 8.

The plasmid pUCTPI-LEU2 was cut with PstI and BamHI to linearize the DNA. The yeast sequences were then isolated from the pUC13 sequences by electrophoresis and gel purification. The yeast DNA portion depicted in FIG. 8 was used to transform *S. cerevisiae* strain E2-7B (ATCC No. 20689), which is deficient for LEU2, in order to "disrupt" the TPI1 chromosomal gene (Rothstein, ibid.). Leu$^+$ transformants were selected on a synthetic (modified Wickerham's) medium (Mortimer and Hawthorne, in Rose and Harrison, eds., *The Yeasts* vol. 1, 385-460, Academic Press, 1969) which contained 3% glycerol and 1% lactate (neutralized to pH 7), 1M Sorbitol, and no leucine. The transformants were screened for a TPI deficiency by their inability to grow on YEP-Dextrose. One tpi$^-$ transformant was found among the first 99 transformants screened. This strain was designated as E2-7BΔtpi#29 (hereinafter Δtpi#29). Δtpi#29 grew on YEP-3% Glycerol-1% Lactate but not on YEP-Dextrose. Enzyme assays (Clifton, et al., *Genetics* 88: 1-11, 1980) were run on crude cellular extracts and confirmed that Δtpi#29 was lacking detectable levels of triose phosphate isomerase activity.

Δtpi#29 may be crossed to other yeast strains to form diploids that are heterozygous for the tpi$^-$ deletion. Such diploids may be sporulated so that other strains deficient for triose phosphate isomerase can be generated. For example, Δtpi#29 has been crossed to E8-10A (MATα leu2) (a spore segregant of the cross E2-7BxGK100[ATCC 20669]) to form the diploid, E11. This diploid has been sporulated to generate the haploid descendant, E11-3C, which has the following genotype: MATα pep4-3 tpi1. E11-3C has been crossed back to Δtpi#29 to form a diploid, E18, that is homozygous for the tpi1 deletion. E18 may be preferred over Δtpi#29 as a host strain for a plasmid because it has no amino acid requirements, has larger cells, and grows faster. These tpi$^-$ strains are deleted for the genetic material which codes for the glycolytic function and are, therefore, expected to be nonreverting (i.e., stable) mutants.

C. Transformation of the POT1 gene into *S. cerevisiae* tpi$^-$ deletion strains.

The plasmids pFPOT and pFATPOT were transformed into Δtpi#29 and related tpi$^-$ deletion strains. The yeast mutants were grown aerobically overnight to late log phase in YEP-2% Galactose at 30°. Transformation conditions were as described by Beggs (ibid.), except that the cells were allowed to recover at 30° for 1-2 hours in 1M Sorbitol containing YEP-3% Glycerol-1% Lactate or YEP-2% Galactose, instead of YEP-Dextrose, before plating the cells in top agar. The top agar and plates contained synthetic, modified Wickerham's medium with 1M Sorbitol and 2% Dextrose. After three days at 30°, transformants were visible and were picked out of the agar for replating onto YEPD. Thereafter, the transformants were maintained on YEPD or other complex media containing dextrose.

Strain E18 transformed with pFATPOT was designated ZYM-3. It has been deposited with ATCC under accession number 20699.

Stability of pFPOT and pFATPOT on complex media. To study plasmid stability, colonies from a single cell were inoculated into tubes containing YEPD and allowed to grow to a total population of $10^9$ cells (approximately 30 divisions). The yeast cells were sonicated to break up clumps, diluted to appropriate numbers, and plated onto YEP-2% Galactose or YEP-2% Glycerol-1% Lactate, which allows the growth of tpi− cells (with or without the plasmids carrying the POT1 gene). The colonies which arose on YEP-Galactose were then replica plated onto YEPD to screen for the loss of the plasmid (i.e., tpi− cells which have lost the POT1-containing plasmid will not grow on dextrose). The results, summarized in Table 2, indicate that the pFPOT and pFATPOT plasmids are stable in the yeast tpi− deletion strains. They are surprisingly much more stable than yeast plasmids containing centromeres. Centromere-bearing plasmids (which are low in copy number) are among the most stable plasmids reported for yeast and are generally lost at a frequency of around 1% of cells per division on complex media (see Murray and Szostak, ibid., for a review of centromere plasmid stability). As Table 2 indicates, the POT1 plasmids described herein are lost at a frequency of less than 1% after 30 divisions on complex media in tpi− deletion strains.

D. Expression of human alpha-1-antitrypsin in *S. cerevisiae* using POT1 plasmids To test the use of the POT1 plasmids for enhancing expression of foreign proteins in a transformed yeast, plasmids pFATPOT and pFAT5 were used to transform *S. cerevisiae* strains Δtpi#29 and E2-7B respectively. Transformed cells were selected in leucineless media containing dextrose. Cultures were grown at 30° to an O.D.$_{600}$ of 3–4. Cell extracts were prepared and assayed for AT as described in Example 5.

AT produced by pFATPOT/Δtpi#29 represented 4–6% of total soluble protein. AT produced by pFAT5-/E2-7B represented 2–3% of total soluble protein.

Although plasmid copy numbers are difficult to accurately measure and represent a population average, empirical observations of gene product quantities provide an indication of relative plasmid levels, given that the expression unit (promoter, gene of interest, terminator) remains the same. pFATPOT therefore appears to be functionally greater in number than pFAT5, from which it was derived. Because the two transformed strains are nearly identical genetically (Δtpi#29 being derived from E2-7B by plasmid-directed mutagenesis) and were grown under the same conditions, these results are indicative of the value of the herein-described stable plasmid expression system over previously described vectors.

TABLE 1

STABILITY OF CDC4 PLASMIDS

| Isolate Number | Total Colonies[a] | CDC4[+b] | Trp[+c] | Leu[+d] |
|---|---|---|---|---|
| 1(BELL 1) | 123 | 123 | 123 | 123 |
| 2 | 80 | 80 | 80 | 80 |
| 3 | 83 | 80 | 80 | 83 |
| 4 | 96 | 96 | 96 | 96 |
| 5 | 88 | 88 | 88 | 88 |
| 6 | 115 | 115 | 115 | 115 |

[a] Cells were grown in liquid complex medium (YEPD) at 25° for 30 generations, then plated on YEPD at 25°.
[b] Cells were replica plated to YEPD at 37°. Cells lacking an intact CDC4 gene failed to grow at this (restrictive) temperature.
[c] Cells were replica plated to medium lacking tryptophan.
[d] Cells were replica plated to medium lacking leucine.

TABLE 2

STABILITY OF POT1 PLASMIDS VS. pTPIC10

| Experiment | Plasmid/Strain | Total Colonies[a] | TPI[+b] | % Loss[c] |
|---|---|---|---|---|
| 1 | pTPIC10/Δtpi#29 | 234 | 163 | 30.3 |
| 2 | pFPOT/Δtpi#29 | 308 | 308 | 0 |
| 3 | pFATPOT/Δtpi#29 | 471 | 471 | 0 |
| 4 | pFATPOT/E18(ZYM-3) | 1104 | 1104 | 0 |
| 5 | pFATPOT/E18(ZYM-3) | 634 | 632 | 0.32 |
| 6 | pFATPOT/Δtpi#29 | 426 | 426 | 0 |
| 2–6 | pooled data | 2943 | 2941 | 0.07 |

[a] The plasmid/strain combinations were grown on YEPD plates until easily visible colonies of approximately $10^4$ to $10^5$ cells were seen. These colonies were used to inoculate 6 ml of YEPD liquid medium. The cultures were grown aerobically overnight to a cell density of 1–3 × $10^8$ cells/ml and were plated onto YEP-2% Glycerol-1% Lactate or YEP-2% Galactose. Each of these media would allow tpi− strains to grow, although the resulting tpi− colonies arose more slowly than tpi+ colonies. Only 100–300 cells were distributed on each plate so that each colony (whether tpi− or tpi+) would be countable.
[b] The colonies were replica plated onto synthetic media containing dextrose at a 2% final concentration. Cells which had lost the triose phosphate isomerase gene on the plasmids were unable to grow.
[c] The "% Loss" represents the frequency of cells that had lost the plasmid after nearly 30 divisions in YEPD. The pooled data for experiments 2 to 6 indicate that the POT1 plasmids are extremely stable over these many divisions and are lost at a combined frequency well below 1% in 30 cell doublings.

EXAMPLE 3

Preparation of Plasmid C1/1

C1/1 was constructed from plasmid pJDB248 (Beggs, J., *Nature* 275, 104–109 (1978)). The pMB9 sequences were removed from pJDB248 by partial digestion with Eco RI and were replaced by pBR322 DNA which was cut with Eco RI. The restriction map of C1/1 is given in FIG. 6. The C1/1 plasmid contains the entire 2-micron DNA from yeast (*S. cerevisiae*), with a pBR322 insertion at an EcoRI site. It also contains the LEU2 gene.

EXAMPLE 4

Preparation of Plasmid pFAT5

The gene coding for the predominant form of human alpha-1-antitrypsin (AT) was isolated from a human liver cDNA library by conventional procedures using the baboon sequence (Kurachi et al., *Proc. Natl. Acad. Sci. USA* 78: 6826–6830, 1980; and Chandra et al., *Biochem. Biophys. Res. Comm.* 103: 751–758, 1981) as a DNA hybridization probe. The library was constructed by inserting human liver cDNA into the PstI site of the plasmid pBR322 (Bolivar et al., *Gene* 2: 95–113, 1977). The AT gene was isolated from the library as a 1500 base pair (bp) PstI fragment. This fragment was inserted into the PstI site of pUC13 to produce the plasmid pUCα1. In pUCα1, the AT sequence is flanked on the 3' end by XbaI and EcoRI sites in the polylinker.

The TPI terminator was purified from plasmid pFG1 (Alber and Kawasaki, ibid.) as a XbaI-EcoRI fragment of approximately 700 bp and inserted into pUCα1 which had been cleaved with XbaI and EcoRI. This construct was then cut with EcoRI, and oligonucleotide linkers (sequence:

```
AATTCATGGAG
    GTACCTCCTAG)
``` were added, in multiple linked copies, to provide a BamHI site to the 3' end of the TPI terminator. The resultant plasmid is known as BAT5.

The TPI promoter fragment was obtained from plasmid pTPIC10 (Alber and Kawasaki, ibid). This plasmid was cut at the unique KpnI site, the TPI coding region was removed with Ba131 exonuclease, and an EcoRI linker (sequence: GGAATTCC) was added to the 3' end of the promoter. Digestion with BglII and EcoRI yielded a TPI promoter fragment having BglII and EcoRI sticky ends. This fragment was then joined to plasmid YRp7' (Stinchcomb, et al. *Nature* 282: 39–43, 1979) which had been cut with BglII and EcoRI. The resulting plasmid, TE32, was cleaved with EcoRI and BamHI to remove a portion of the tetracycline resistance gene. The linearized plasmid was then recircularized by the addition of the above described EcoRI-BamHI linker to produce plasmid TEA32. TEA32 was then cleaved with BglII and BamHI, and the TPI promoter was purified as a fragment of approximately 900 bp.

Figure 7:
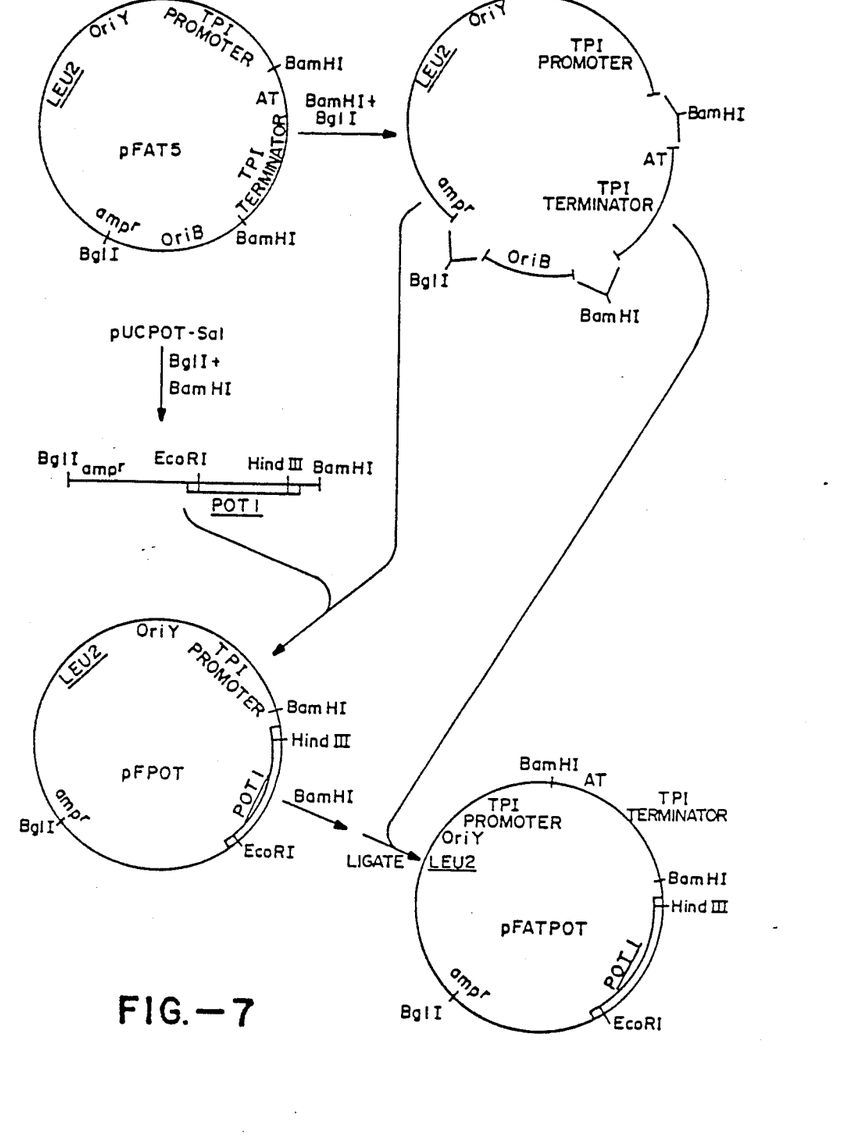
FIG. 7 illustrates the construction of the plasmid pFATPOT.

To construct plasmid pFAT5, plasmid C1/1 was linearized with BamHI, and was joined to the 900 bp TPI promoter fragment from TEA32. The resulting construct, known as plasmid F, has a unique BamHI site located at the 3' end of the TPI promoter. This plasmid was cut with BamHI and a 2200 bp BamHI fragment, comprising the AT coding sequence and TPI terminator, was purified from BAT5 and inserted into the BamHI site. The resulting plasmid, known as pFAT5, is illustrated in FIG. 7.

EXAMPLE 5

Assay for Alpha-1-Antitrypsin

As a control, 10 microliters (1 microgram) of a solution of 100 microgram/ml trypsin, 100 microgram (100 microliters) of bovine serum albumin and 100 microliters of 0.05 molar TRIS, pH 8.0 buffer containing 1mM benzoylargininoyl-p-ni-troanilide were mixed, and the increase in absorbance at 405 nm was measured over time in a spectrophotometer. The absorbance value of this solution was used as a standard for 100% trypsin activity. All assayed samples contain equal concentrations of substrate and bovine serum albumin.

What is claimed is:

1. A DNA construct comprising a yeast CDC4 gene which complements a deficiency in a microorganism host cell, said deficiency being in a function necessary for normal cell growth in a complex medium not containing antibiotics or heavy metals and not depleted of specific nutrients, and a DNA sequence coding for alpha-1-antitrypsin, wherein said gene can function as a selectable marker in a host cell transformed with said construct to allow normal growth of said transformed cell in said medium.

2. A transformant strain containing a DNA construct according to claim 1.

3. A method for producing alpha-1-antitrypsin in a microorganism host cell having a deficiency in a function necessary for normal cell growth on complex media comprising the steps of:
   (a) transforming said host cell with a DNA molecule comprising a yeast CDC4 gene which complements said deficiency and a sequence coding for alpha-1-antitrypsin;
   (b) culturing the cells from step (a) under normal growth conditions in a growth medium not containing antibiotics or heavy metals and not depleted of specific nutrients, whereby said gene functions as a selectable marker for cells transformed with said DNA molecule.

4. A method for producing alpha-1-antitrypsin in a host cell having a deficiency in a function necessary for normal cell growth on complex media comprising the steps of:
   (a) transforming said host cell with a DNA molecule comprising a *Schizosaccharomyces pombe* triose phosphate isomerase gene which complements said deficiency and a sequence coding for alpha-1-antitrypsin;
   (b) culturing the cells from step (a) under normal growth conditions in a growth medium not containing antibiotics or heavy metals and not depleted of specific nutrients, whereby said gene functions as a selectable marker for cells transformed with said DNA molecule.

5. A DNA construct comprising a *Schizosaccharomyces pombe* triose phosphate isomerase gene which complements a deficiency in a microorganism host cell, said deficiency being in a function necessary for normal cell growth in a complex medium not containing antibiotics or heavy metals and not depleted of specific nutrients, and a DNA sequence coding for alpha-1-antitrypsin, wherein said gene can function as a selectable marker in a host cell transformed with said construct to allow normal growth of said transformed cell in said medium.

6. A method according to claim 3 wherein said gene is from a cell species different from said host cell.

* * * * *